(12) United States Patent
Daum et al.

(10) Patent No.: US 7,155,280 B2
(45) Date of Patent: Dec. 26, 2006

(54) RATE-ADAPTIVE PACEMAKER WITH COMPENSATION FOR LONG-TERM VARIATIONS IN AVERAGE EXERTION LEVEL

(75) Inventors: Douglas R. Daum, Oakdale, MN (US); Quan Ni, Shoreview, MN (US); Zoe Harris, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 624 days.

(21) Appl. No.: 10/286,379

(22) Filed: Nov. 1, 2002

(65) Prior Publication Data

US 2004/0088016 A1    May 6, 2004

(51) Int. Cl.
*A61N 1/365* (2006.01)

(52) U.S. Cl. .......................... 607/19; 607/17

(58) Field of Classification Search ........... 607/17–27
See application file for complete search history.

(56) References Cited

U.S. PATENT DOCUMENTS

| | | | |
|---|---|---|---|
| 4,702,253 A * | 10/1987 | Nappholz et al. ............ 607/20 |
| 4,922,930 A | 5/1990 | Adkins et al. ............ 128/419 |
| 5,014,704 A * | 5/1991 | Alt ............................. 607/19 |
| 5,282,839 A | 2/1994 | Roline et al. ................. 607/19 |
| 5,300,092 A | 4/1994 | Schaldach .................... 607/18 |
| 5,404,877 A * | 4/1995 | Nolan et al. ................. 600/484 |
| 5,441,524 A * | 8/1995 | Rueter et al. ................. 607/18 |
| 5,476,483 A | 12/1995 | Bornzin et al. .............. 607/17 |
| 5,514,162 A | 5/1996 | Bornzin et al. .............. 607/19 |
| 5,645,576 A | 7/1997 | Limousin et al. ............. 607/19 |
| 5,690,687 A * | 11/1997 | Hansen ........................ 607/17 |
| 5,733,312 A | 3/1998 | Schloss et al. ............... 607/17 |
| 5,814,087 A | 9/1998 | Renirie ........................ 607/21 |
| 5,861,011 A | 1/1999 | Stoop .......................... 607/25 |
| 5,957,957 A | 9/1999 | Sheldon ....................... 607/17 |
| 6,044,297 A | 3/2000 | Sheldon et al. .............. 607/17 |
| 6,058,328 A | 5/2000 | Levine et al. ................ 607/14 |
| 6,128,534 A | 10/2000 | Park et al. .................... 607/17 |
| 6,161,041 A | 12/2000 | Stoop et al. .................. 607/14 |
| 6,161,042 A * | 12/2000 | Hartley et al. ............... 607/20 |
| 6,473,646 B1 | 10/2002 | Sun et al. ..................... 607/27 |
| 6,490,485 B1 | 12/2002 | Sun et al. ..................... 607/20 |

\* cited by examiner

*Primary Examiner*—George R. Evanisko
*Assistant Examiner*—Alyssa M. Alter
(74) *Attorney, Agent, or Firm*—Schwegman, Lundberg, Woessner & Kluth, P.A.

(57) ABSTRACT

A rate-adaptive pacemaker is disclosed in which a sensor-indicated rate is calculated by adding a function of the measured exertion level to a programmed lower rate limit. In the case where the function of the measured exertion level is the difference between a short-term average and a long-term average of the measured exertion level, the lower rate limit is modulated as a function of the long-term average of the measured exertion level and maximum and minimum values of the long-term average of the measured exertion level during a defined extended time period.

10 Claims, 3 Drawing Sheets

RATE-ADAPTIVE PACEMAKER WITH COMPENSATION FOR LONG-TERM VARIATIONS IN AVERAGE EXERTION LEVEL

FIELD OF THE INVENTION

This invention pertains to systems and methods for cardiac rhythm management. In particular, the invention relates to a system and method for automatically adjusting the operating parameters of a rate-adaptive cardiac pacemaker.

BACKGROUND

A conventional cardiac pacemaker is an implantable battery-powered electronic device that responds to sensed cardiac events and elapsed time intervals by changing its functional states so as to properly interpret sensed data and deliver pacing pulses to the heart at appropriate times. The pacing pulses are delivered through a lead made up of electrodes on a catheter or wire that connects the pacemaker to the heart. Modern pacemakers are typically programmable so that they can operate in any mode which the physical configuration of the device will allow. Such modes define which heart chambers are paced, which chambers are sensed, and the response of the pacemaker to a sensed P wave or R wave. A three-letter code is used to designate a pacing mode where the first letter refers to the paced chamber(s), the second letter refers to the sensed chamber(s), and the third letter refers to the response. Additional sensing of physiological data allows some pacemakers to change the rate at which they pace the heart in accordance with some parameter correlated to metabolic demand. Such pacemakers, which are the primary subject of the present invention, are called rate-adaptive pacemakers.

The most common condition for which pacemakers are used is the treatment of bradycardia. Permanent pacing for bradycardia is indicated in patients with symptomatic bradycardia of any type as long as it is likely to be permanent or recurrent and is not associated with a transient condition from which the patient may recover. Atrio-ventricular conduction defects (i.e., AV block) that are fixed or intermittent and sick sinus syndrome represent the most common indications for permanent pacing. In chronotropically competent patients in need of ventricular pacing, atrial triggered modes such as DDD or VDD are desirable because they allow the pacing to track the physiologically normal atrial rhythm, which causes cardiac output to be responsive to the metabolic needs of the body. Atrial triggering modes are contraindicated, however, in patients prone to atrial fibrillation or flutter or in whom a reliable atrial sense cannot be obtained. In the former case, the ventricles will be paced at too high a rate. Failing to sense an atrial P wave, on the other hand, results in a loss of atrial tracking which can lead to negative hemodynamic effects because the pacemaker then reverts to its minimum ventricular pacing rate. In pacemaker patients who are chronotropically incompetent (e.g., sinus node dysfunction) or in whom atrial-triggered modes such as DDD and VDD are contraindicated, the heart rate is determined solely by the pacemaker in the absence of intrinsic cardiac activity. That heart rate is determined by the programmed escape intervals of the pacemaker and is referred to as the lower rate limit or LRL.

Pacing the heart at a fixed rate as determined by the LRL setting of the pacemaker, however, does not allow the heart rate to increase with increased metabolic demand. Cardiac output is determined by two factors, the stroke volume and heart rate, with the latter being the primary determinant. Although stroke volume can be increased during exercise, the resulting increase in cardiac output is usually not sufficient to meet the body's metabolic needs unless the heart rate is also increased. If the heart is paced at a constant rate, as for example by a VVI pacemaker, severe limitations are imposed upon the patient with respect to lifestyle and activities. It is to overcome these limitations and improve the quality of life of such patients that rate-adaptive pacemakers have been developed. Rate-adaptive pacemakers operate so as to vary the lowest rate at which the heart is allowed to beat in accordance with one or more physiological parameters related to metabolic demand.

The body's normal regulatory mechanisms act so as to increase cardiac output when the metabolic rate is increased due to an increased exertion level in order to transport more oxygen and remove more waste products. One way to control the rate of a pacemaker, therefore, is to measure the metabolic rate of the body and vary the pacing rate in accordance with the measurement. Metabolic rate can effectively be directly measured by, for example, sensing blood pH or blood oxygen saturation. Practical problems with implementing pacemakers controlled by such direct measurements, however, have led to the development of pacemakers that are rate-controlled in accordance with physiological variables that are indirectly reflective of the body's metabolic rate such as body temperature, ventilation rate, or minute ventilation. Minute ventilation varies almost linearly with aerobic oxygen consumption during exercise up to the anaerobic threshold and is the physiological variable that is most commonly used in rate-adaptive pacemakers to reflect the exertion level of the patient. An even more indirect indication of metabolic rate is provided by the measurement of body activity or motion. Body activity is correlated with metabolic demand because such activity requires energy expenditure and hence oxygen consumption. An activity-sensing pacemaker uses a piezoelectric sensor or accelerometer inside the pacemaker case that responds to vibrations or accelerations by producing electrical signals proportional to the patient's level of physical activity.

However exertion level is measured, it may be desirable to adjust the pacing rate based upon a function of the measured exertion level in order to compensate for sensor drift and prevent overpacing. Such a function of the measured exertion level would usually involve computing an average exertion level over a specified time period. Because of natural variations in the average exertion level, however, adjusting the pacing rate in this manner may result in sub-optimal pacing.

SUMMARY OF THE INVENTION

The present invention may be incorporated in a rate-adaptive cardiac pacemaker that is programmed to deliver pacing pulses in accordance with a demand pacing mode at a sensor-indicated rate equal to a lower rate limit plus a function of the measured exertion level multiplied by a rate-response factor. The pacemaker may then be further programmed to compute the function of the measured exertion level as the amount, if any, by which a short-term average of the measured exertion level exceeds a long-term average of the measured exertion level. In order to prevent sub-optimal pacing due to circadian variations in the measured exertion level parameter, the lower rate limit may be modulated as a function of the long-term average of the measured exertion level and maximum and minimum values of the long-term average of the measured exertion level during a defined extended time period. In an alternative approach, the function of the measured exertion level is computed as the amount, if any, by which a short-term average of the measured exertion level exceeds the minimum value of a long-term average of the measured exertion level that occurs during a defined extended time period.

DETAILED DESCRIPTION

Figure 1:
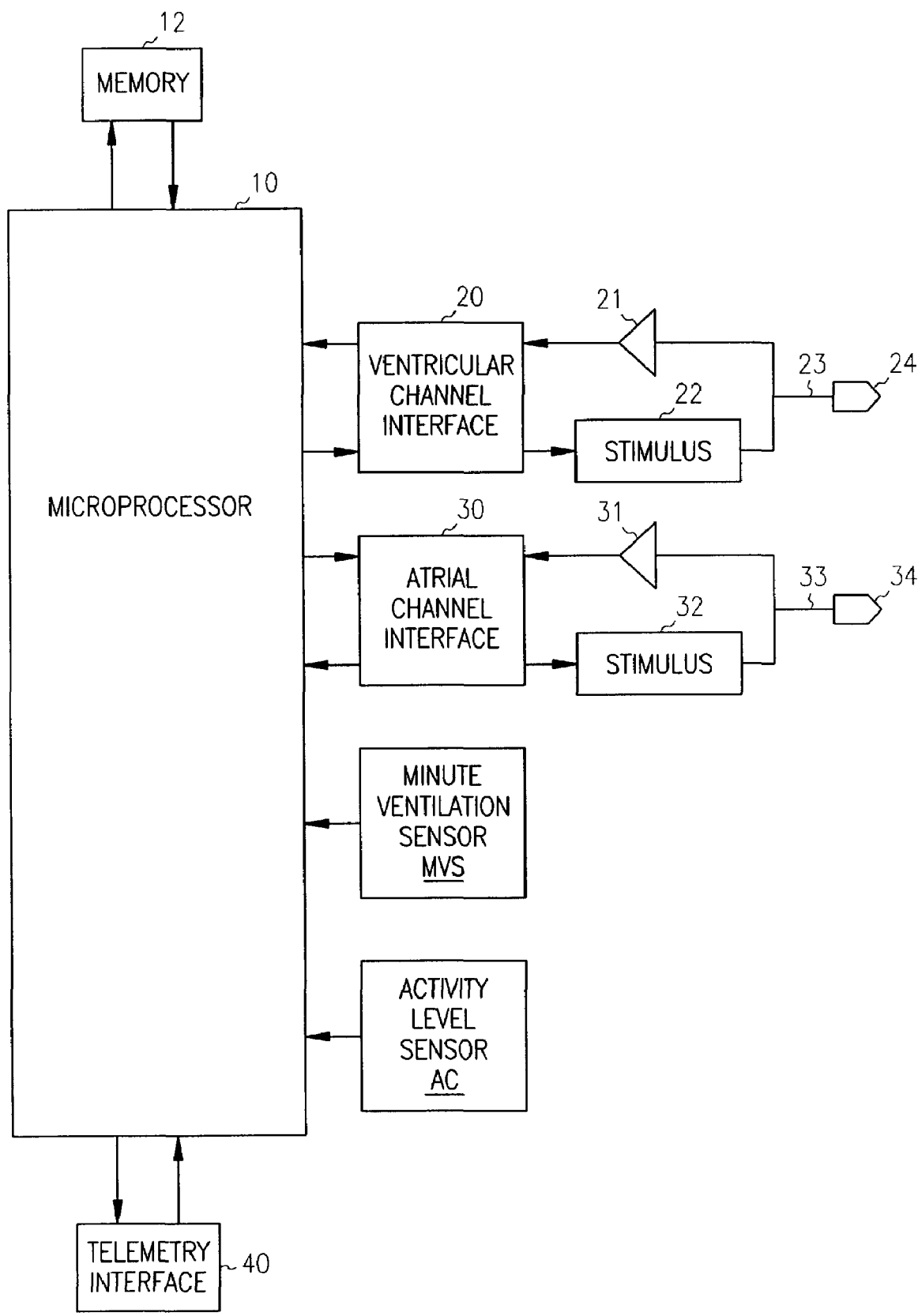
FIG. 1 is a diagram of a rate-adaptive pacemaker.

A particular implementation of a rate-adaptive pacemaker is shown in FIG. 1. As used herein, the term pacemaker should be taken to mean any cardiac rhythm management device with a pacing functionality including an implantable cardioverter/defibrillator that includes a pacemaker. A pacemaker controller senses cardiac events through a sensing channel and outputs pacing pulses to the heart via a pacing channel in accordance with a programmed pacing mode. A microprocessor 10 serves as the controller in this embodiment and communicates with a memory 12 via a bidirectional data bus. The memory 12 typically comprises a ROM or RAM for program storage and a RAM for data storage. The pacemaker has atrial sensing and pacing channels comprising electrode 34, lead 33, sensing amplifier 31, pulse generator 32, and an atrial channel interface 30 which communicates bidirectionally with a port of microprocessor 10. The device also has ventricular sensing and pacing channels comprising electrodes 24, lead 23, sensing amplifier 21, pulse generator 22, and ventricular channel interface 20. For each channel, the same lead and electrode are used for both sensing and pacing. The channel interfaces 20 and 30 include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. A telemetry interface 40 is also provided for communicating with an external programmer. A minute ventilation sensor MVS and an accelerometer AC are employed to sense the minute ventilation and body activity, respectively. As explained below, the minute ventilation sensor includes a pair of current source electrodes and a pair of voltage sense electrodes for measuring transthoracic impedance. An example of such a minute ventilation sensor is described in U.S. Pat. No. 6,161,042, assigned to the assignee of the present application and hereby incorporated by reference in its entirety. The pacemaker uses the sensed minute ventilation and/or the accelerometer signal to adjust the rate at which the pacemaker paces the heart in the absence of a faster intrinsic rhythm. The microprocessor 10 executes programmed instructions that implement various pacing and rate-adaptive algorithms.

Figure 2:
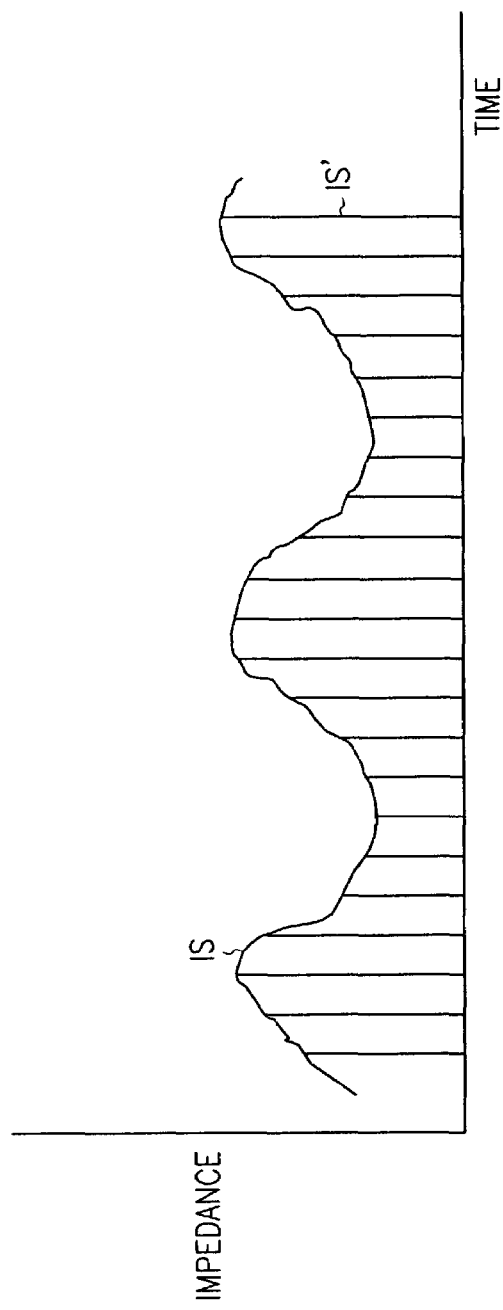
FIG. 2 shows an example of an impedance signal.

The electrical impedance of a conductive path between two points that includes part of the thoracic cavity varies in accordance with a subject's respiration. If the voltage between two voltage sense electrodes in the thoracic cavity were measured while a constant excitation current flows between two current source electrodes, a voltage signal corresponding to the impedance between the sense electrodes would be produced. FIG. 2 shows such a transthoracic impedance signal IS that represents the time-varying impedance between the two sense electrodes while the subject breathes as would be generated by a continuous excitation current. However, it is preferable to inject the excitation current in the form of a pulse train with narrow pulse-widths in order to conserve battery energy. The impedance signal produced at the voltage sense electrodes is then a pulse train at the excitation frequency that is amplitude-modulated by the impedance signal IS. The resulting signal can also be regarded as a discrete-time impedance signal IS' with each signal value representing samples of the continuous impedance signal IS taken at a sampling rate equal to the excitation frequency.

Before deriving the minute ventilation, the impedance signal is filtered to remove both low and high frequency components. The impedance signal thus filtered will be referred to as the ventilation signal. The low frequency components of the impedance signal include both a zero frequency or DC voltage that represents the impedance at full expiration and lower frequency voltages that represent impedance changes due to the slow changes in residual volume of the lungs that occur as the subject alternates between deep and shallow breathing. The high frequency components of the impedance signal include both voltages representing impedance changes resulting from the changes in ventricular blood volume as the heart beats and voltages caused by additional current fields produced from external noise sources. These components can be removed with a bandpass filter or a combination of low-pass and high-pass filtering. Exemplary lower and upper cutoff frequencies for such filtering could be on the order of 0.1 and 1 Hz, respectively, which thus define a ventilation band in which the ventilation signal is found. After filtering the impedance signal to remove the unwanted frequency components, the resulting ventilation signal is directly reflective of the movement of air into and out of the lungs. The minute ventilation can then be derived from the ventilation signal by a number of different methods. For example, the signal can be filtered to derive both a respiratory rate and an average tidal volume, the product of which is the minute ventilation. Alternatively, successive peak-to-peak transitions of the signal, each of which represents the quantity of air inspired during a breath, can be summed over a specified period of time to result in a minute ventilation value.

Figure 3:
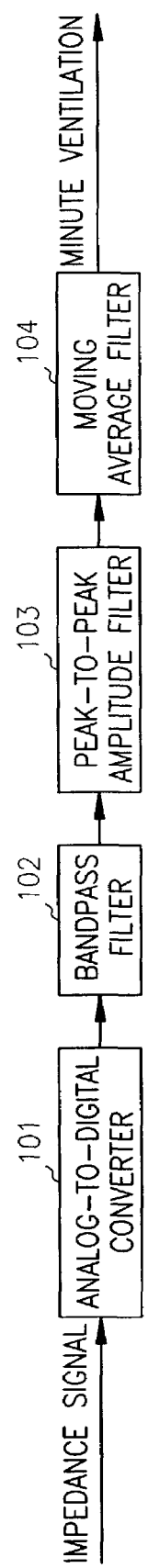
FIG. 3 is a diagram of exemplary functional circuitry for deriving minute ventilation from an impedance signal.

The impedance signal can be processed in either the analog or digital domain or with a combination of digital and analog processing in order to compute the minute ventilation. For example, the discrete time signal IS' generated by the voltage sense electrodes when excitatory current pulses are output can be low-pass filtered to remove the pulse train carrier waveform. The resulting analog waveform can then be further filtered to derive the ventilation signal as described above. The additional filtering can be performed in the analog domain, or the analog signal can be sampled and converted into a digital signal that can be processed in the digital domain. Alternatively, the values of the discrete time signal IS', which correspond to measurements of the voltage between the voltage sense electrodes during an excitation current pulse, can be digitized and processed entirely in the digital domain. FIG. 3 is a block diagram showing one example of how the impedance signal IS' may be further processed either in the analog or digital domain to derive the minute ventilation. The components of FIG. 3 may be implemented as code executed by the controller or by dedicated hardware components. A digital bandpass filter 102 (or, equivalently, a combination of low and high pass filters) filters the impedance signal IS' to generate the ventilation signal VS. A peak-to-peak transition filter 103 then derives successive amplitudes of peak-to-peak transitions of the VS waveform that represent inspirations. Each such peak-to-peak transition amplitude is proportional to the tidal volume during a single breath. The successive peak-to-peak transition amplitudes are then filtered by a moving average filter 104 with a specified averaging period to derive a signal proportional to the minute ventilation.

In rate-adaptive pacemakers that vary the pacing rate in accordance with a measured exertion level, the control system is generally implemented as an open-loop controller that maps a particular exertion level to one particular target heart rate, termed the sensor-indicated rate or SIR. The SIR is the rate at which the heart (either the atria or ventricles) is paced in the absence of faster intrinsic activity. The mapping is accomplished by a rate-response curve which is typically a linear function (i.e., a straight line), but could also be some non-linear function as well such as a dual-slope curve or exponential curve. The rate-response curve is then defined with minimum and maximum target heart rates. A minimum target heart rate for a patient can be ascertained clinically as a heart rate adequate to sustain the patient at rest, and the programmed lower rate limit or LRL of the pacemaker is set to this rate. A maximum allowable pacing rate or MPR is set to a heart rate defined with a formula that depends on the patient's age. The rate-response curve then maps a resting exertion level to the minimum heart rate or LRL and maps the maximum exertion level attainable by the patient, termed the maximum exercise capacity, to the maximum allowable heart rate. The responsiveness of the control system, defined as how the sensor-indicated rate changes with a given change in exertion level, depends upon the slope of the rate-response curve (or slopes in the case of a dual-slope curve).

Figure 4:
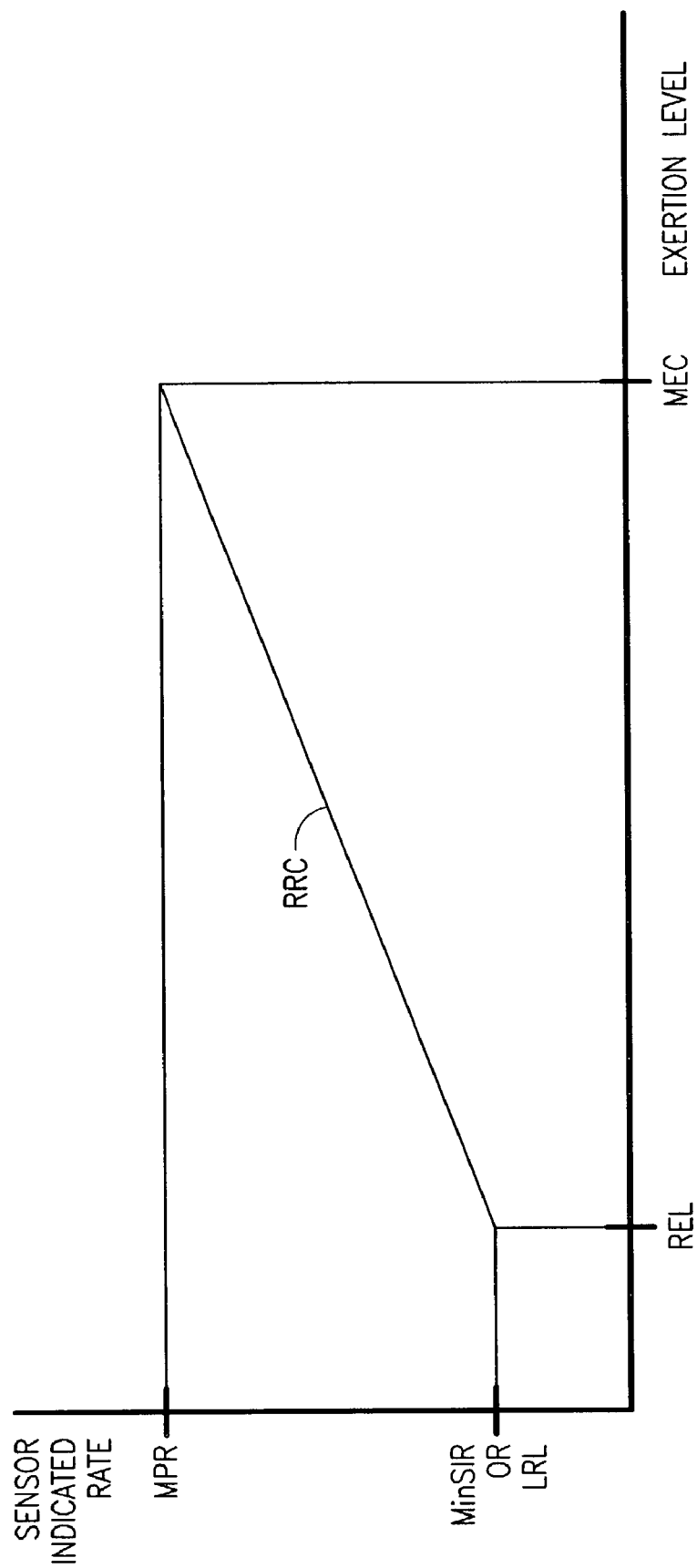
FIG. 4 depicts a rate-response curve.

An example of a rate-response curve RRC is shown in FIG. 4. Other embodiments may use a dual-slope curve or a non-linear curve. A change in exertion level as determined from a minute ventilation measurement causes a proportional change in the sensor-indicated rate in accordance with the slope of the curve, termed the response factor RF. The sensor-indicated rate is then used by the pacemaker to pace the heart in accordance with a programmed pacing mode. As shown in the figure, the rate response curve maps a resting exertion level REL to a minimum target rate MinSIR which corresponds to the programmed LRL of the pacemaker. The maximum pacing rate MPR is the maximum rate at which the pacemaker is allowed to pace the heart and is mapped to by the rate response curve from the maximum exertion level the patient is expected to be able to reach, referred to as the maximum exercise capacity MEC. The sensor-indicated rate is then calculated from the measured exertion level EXL as:

$$SIR = LRL + RF * EXL$$

In the case where minute ventilation is used as a measure of exertion level, the sensor-indicated rate is computed as:

$$SIR = LRL + RF * MV$$

where MV is the measured minute ventilation. The SIR is thus always greater or equal to the LRL, and is limited by the programmed MPR.

Because of the possibility of long-term drift of the exertion level sensor, there is a risk that a patient could be subjected to dangerous overpacing for an extended period of time, where the heart is paced at too high a rate relative to the patient's actual exertion level. This problem can occur with any kind of exertion level sensor, but may especially be of concern with impedance sensors used to measure minute ventilation. In order to eliminate this situation, the measured exertion level used in the equation above for calculating the SIR may be calculated as the difference between a short-term average and a long-term average of the exertion level signal. That is:

$$EXL = EXL_{sta} - EXL_{lta}$$

or, in the case of minute ventilation, $$MV = MV_{sta} - MV_{lta}$$

where $MV_{sta}$ and $EXL_{sta}$ are the short-term averages, and $MV_{lta}$ and $EXL_{lta}$ are the long-term averages. Exemplary periods for calculation of the short-term and long-term averages are 30 seconds and 2 hours, respectively. The equations then become:

$$EXL = EXL_{30s} - EXL_{2h}$$

and $$MV = MV_{30s} - MV_{2h}$$

A problem that arises when the exertion level is computed as a difference between short-term and long-term averages is the natural circadian rhythm of the measured exertion level parameter. Such a circadian rhythm occurs with respect to minute ventilation, as well as possible other exertion level parameters. Studies of representative subjects have shown that the baseline minute ventilation level decreases at night (presumably while the subject sleeps) and then increases during the day (while the subject is presumably awake and active). It is common for the maximum $MV_{2h}$ during the day to be twice as large as the minimum $MV_{2h}$. This has important implications for the sensor response of a rate-adaptive pacemaker using the difference between a short-term and a long-term average of minute ventilation as the exertion level parameter. Because the MV used to calculate the SIR in the evening is derived with a long-term average of the minute ventilation that is higher during the day than at night, an activity that takes the same amount of exertion as measured by the $MV_{30s}$ or other short-term average will yield a higher SIR during the morning than during the evening. This is clearly suboptimal pacemaker operation since a given exertion level should result in the same pacing rate whenever it occurs.

In order to compensate for the variations in the long-term average of exertion level used to compute the sensor-indicated rate, the lower rate limit may be modulated in accordance with how the long-term average of exertion level compares with minimum and maximum values of the long-term average during a defined extended time period. In one embodiment, the LRL is modulated between minimum and maximum values according to the fraction of the range between minimum and maximum values of the long-term average exertion level during the extended time period that is represented by the current long-term average exertion level. An exemplary formula for the calculation is:

$$LRL = LRL_{min} + (LRL_{max} - LRL_{min}) * (EXL_{lta} - EXL_{ltaMin}) / (EXL_{ltaMax} - EXL_{ltaMin})$$

where $LRL_{min}$ and $LRL_{max}$ are programmed minimum and maximum values, respectively, for the LRL, $EXL_{lta}$ is the long-term average of the measured exertion level, $EX_{ltaMin}$ is the minimum value of $EXL_{lta}$ during the defined extended time period, and $EXL_{ltaMax}$ is the maximum value of $EXL_{lta}$ during the defined extended time period. In a more specific implementation, the exertion level parameter is minute ventilation, the defined extended time period is 24 hours, the long-term averaging period is 2 hours, and the short-term averaging period is 30 seconds. The formula then becomes:

$$LRL=LRL_{min}+(LRL_{max}-LRL_{min})*(MV_{2h}-MV_{2hMin})/(MV_{2hMax}-MV_{2hMin})$$

where $LRL_{min}$ and $LRL_{max}$ are programmed minimum and maximum values, respectively, for the LRL (e.g., 50 and 70 bpm, respectively), $MV_{2h}$ is the 2 hour average of the measured minute ventilation, $MV_{2hMin}$ is the minimum value of $MV_{2h}$ during the 24 hour time period, and $MV_{2hMax}$ is the maximum value of $MV_{2h}$ during the 24 hour time period.

An alternative approach to the problem involves calculating the SIR based upon the difference between the short-term average exertion level and a minimum value of the long-term average exertion level during a defined extended time period. That is, the sensor-indicated rate is calculated as the lower rate limit plus a function of the measured exertion level multiplied by a rate-response factor, where the function of the measured exertion level is the amount, if any, by which a short-term average of the measured exertion level exceeds the minimum value of a long-term average of the measured exertion level that occurs during a defined extended time period. In the case where the exertion level parameter is minute ventilation, the defined extended time period is 24 hours, the long-term averaging period is 2 hours, and the short-term averaging period is 30 seconds, the calculation is:

$$SIR=LRL+RF*(MV_{30s}-MV_{2hMin}) \text{ if } (MV_{30s}-MV_{2hMin}) \text{ is positive,}$$

and $$SIR=LRL \text{ if } (MV_{30s}-MV_{2hMin}) \text{ is negative,}$$

where SIR is the sensor-indicated rate, $MV_{30s}$ is the 30 second average of the measured minute ventilation, and $MV_{2hMin}$ is the minimum value of $MV_{2h}$ during the 24 hour time period.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A cardiac pacemaker, comprising:
   a pacing channel for delivering pacing pulses to a heart;
   an exertion level sensor for measuring a patient's exertion level;
   a controller for controlling the delivery of pacing pulses through the pacing channel in accordance with a programmed mode, wherein the controller is programmed to pace a heart chamber in a demand mode at a sensor-indicated rate equal to a lower rate limit plus a function of the measured exertion level multiplied by a rate-response factor;
   wherein the controller is further programmed to compute the function of the measured exertion level as the amount, if any, by which a short-term average of the measured exertion level exceeds a long-term average of the measured exertion level; and,
   wherein the controller is further programmed to modulate the lower rate limit as a function of the long-term average of the measured exertion level and the maximum and minimum values of the long-term average of the measured exertion level during a defined extended time period, wherein the controller is programmed to modulate the lower rate limit according to the following formula:

$$LRL=LRL_{min}+(LRL_{max}-LRL_{min})*(EXL_{lta}-EXL_{ltaMin})/(EXL_{ltaMax}-EXL_{ltaMin})$$

where LRL is the lower rate limit to be used by the pacemaker, $LRL_{min}$ and $LRL_{max}$ are programmed minimum and maximum values, respectively, for the LRL, $EXL_{lta}$ is the long-term average of the measured exertion level, $EXL_{ltaMin}$ is the minimum value of $EXL_{lta}$ during the defined extended time period, and $EXL_{ltaMax}$ is the maximum value of $EXL_{lta}$ during the defined extended time period.

2. The pacemaker of claim 1 wherein the controller is programmed such that the defined extended time period is 24 hours, the long-term average of the measured exertion level is computed over a period of 2 hours, and the short-term average of the measured exertion level is computed over a period of 30 seconds.

3. The pacemaker of claim 1 wherein the exertion level sensor is a minute ventilation sensor for measuring a patient's minute ventilation.

4. The pacemaker of the claim 1 wherein the exertion level sensor is a minute ventilation sensor for measuring minute ventilation in a patient.

5. The pacemaker of claim 4 wherein the controller is programmed such that the defined extended time period is 24 hours, the long-term and short-term averages of the measured exertion level are computed over periods of 2 hours and 30 seconds, respectively, and the controller is programmed to modulate the lower rate limit according to the following formula:

$$LRL=LRL_{min}+(LRL_{max}-LRL_{min})*(MV_{2h}-MV_{2hMin})/(MV_{2hMax}-MV_{2hMin})$$

where LRL is the lower rate limit to be used by the pacemaker, $LRL_{min}$ and $LRL_{max}$ are programmed minimum and maximum values, respectively, for the LRL, $MV_{2h}$ is the 2 hour average of the measured minute ventilation, $MV_{2hMin}$ is the minimum value of $MV_{2h}$ during the 24 hour time period, and $MV_{2hMax}$ is the maximum value of $MV_{2h}$ during the 24 hour time period.

6. The method of claim 1 wherein the measured exertion level is a patient's minute ventilation.

7. The method of claim 6 wherein the defined extended time period is 24 hours, the long-term and short-term averages of the measured exertion level are computed over periods of 2 hours and 30 seconds, respectively, and the lower rate limit is modulated according to the following formula:

$$LRL=LRL_{min}+(LRL_{max}-LRL_{min})*(MV_{2h}-MV_{2hMin})/(MV_{2hMax}-MV_{2hMin})$$

where LRL is the lower rate limit to be used by the pacemaker, $LRL_{min}$ and $LRL_{max}$ are programmed minimum and maximum values, respectively, for the LRL, $MV_{2h}$ is the 2 hour average of the measured minute ventilation, $MV_{2hMin}$ is the minimum value of $MV_{2h}$ during the 24 hour time period, and $MV_{2hMax}$ is the maximum value of $MV_{2h}$ during the 24 hour time period.

8. A method for operating a cardiac pacemaker, comprising:
   delivering pacing pulses to a heart chamber in a demand mode at a sensor-indicated rate equal to a lower rate limit plus a function of a measured exertion level multiplied by a rate-response factor;

computing the function of the measured exertion level as the amount, if any, by which a short-term average of the measured exertion level exceeds a long-term average of the measured exertion level; and, modulating the lower rate limit as a function of the long-term average of the measured exertion level and maximum and minimum values of the long-term average of the measured exertion level during a defined extended time period, wherein the lower rate limit is modulated according to the following formula:

$$LRL = LRL_{min} + (LRL_{max} - LRL_{min}) * (EXL_{lta} - EXL_{ltaMin}) / (EXL_{ltaMax} - EXL_{ltaMin})$$

where LRL is the lower rate limit to be used by the pacemaker, $LRL_{min}$ and $LRL_{max}$ are programmed minimum and maximum values, respectively, for the LRL, $EXL_{lta}$ is the long-term average of the measured exertion level, $EXL_{ltaMin}$ is the minimum value of $EXL_{lta}$ during the defined extended time period, and $EXL_{ltaMax}$ is the maximum value of $EXL_{lta}$ during the defined extended time period.

9. The method of claim 8 wherein the defined extended time period is 24 hours, the long-term average of the measured exertion level is computed over a period of 2 hours, and the short-term average of the measured exertion level is computed over a period of 30 seconds.

10. The method of claim 8 wherein the measured exertion level is a patient's minute ventilation.

* * * * *